United States Patent [19]

Avar et al.

[11] 3,959,265
[45] May 25, 1976

[54] ORGANIC COMPOUNDS

[75] Inventors: Lajos Avar, Binningen; Kurt Hofer, Munchenstein, both of Switzerland

[73] Assignee: Sandoz Ltd., Basel, Switzerland

[22] Filed: May 7, 1975

[21] Appl. No.: 575,157

[30] Foreign Application Priority Data

May 13, 1974 Switzerland.................... 6492/74

[52] U.S. Cl................................ 260/242; 260/299; 260/45.75 N
[51] Int. Cl.² ................ C07D 231/22; C07F 15/04; C08K 5/34; C07D 231/26
[58] Field of Search............................ 260/242, 299

[56] References Cited
UNITED STATES PATENTS

| | | | |
|---|---|---|---|
| 2,891,070 | 6/1959 | Ledrut................................ | 260/299 |
| 3,808,228 | 4/1974 | Trofimenko.......................... | 260/299 |
| 3,852,297 | 12/1974 | Moser et al........................ | 260/242 |
| 3,901,931 | 8/1975 | Rasherger.......................... | 260/242 |

OTHER PUBLICATIONS

J. Inorg. Chem., (1971), Vol. 33, No. 1, pp. 179–188, Pergamon Press, printed in Great Britain.
Chemical Abstracts, Vol. 53:13136f; Vol. 56:12873h; Vol. 57:382a; Vol. 68:34952f; Vol. 71:129385z and Vol. 79:140168s.

*Primary Examiner*—Donald B. Moyer
*Attorney, Agent, or Firm*—Gerald D. Sharkin; Richard E. Vila; Joseph J. Borovian

[57] ABSTRACT

The present invention concerns novel nickel complexes (I) possessing U.V. stabilizing properties characterized by bearing per molecule 2 monodentate nickel coordinated 1,3-hydrocarbyl-4-(greater than $C_1$)-acyl-pyrazole-5-oxy ligands and one bidentate or two monodentate nickel coordinated primary or secondary amine ligands, and their use as U.V. stabilizers for e.g. plastics materials.

15 Claims, No Drawings

PYRAZOLE NICKEL COMPLEXES AS STABILIZERS FOR ORGANIC MATERIALS

The present invention relates to nickel complexes useful in the stabilization of sensitive material against the degradative effect of ultraviolet (U.V.) light.

Accordingly, the present invention provides nickel complexes (I) possessing U.V. stabilizing properties characterized by bearing per molecule 2 monodentate nickel coordinated 1,3-hydrocarbyl-4-(greater than $C_1$)acyl-pyrazole-5-oxy ligands and one bidentate or two monodentate nickel coordinated primary or secondary amine ligands.

It is to be understood that by the term "(greater than $C_1$)acyl" is meant a keto radical of the formula

It is also to be understood that the secondary amine ligand may be in the form of a nitrogen-containing heterocycle, e.g. a 5 or 6 membered nitrogen containing heterocycle which may additionally contain a further heteroatom such as oxygen, e.g. piperidino, morpholino, pyrrolidino or imidazolidino.

As will be appreciated, whether the amine can serve as a mono- or bidentate ligand will depend on the nature of the amine. For example, hydroxyalkylamines can serve as bidentate ligands.

As will also be appreciated, the 4-acyl-pyrazole-(5)-oxy moiety may bear substituents on the 1,3-hydrocarbyl substituents attached to the pyrazole ring which do not adversely affect the U.V. stabilizing properties or stability of the complexes. The selection of such substituents forms part of the general knowledge in the U.V. stabilizer art.

A preferred group of complexes of the invention are the complexes of formula Ia,

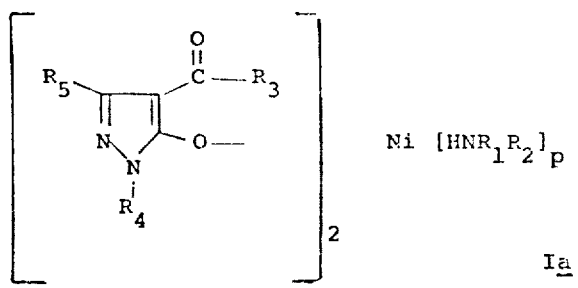

wherein either $R_1$ is hydrogen, alkyl ($C_1$-$C_8$, preferably $C_1$ or $C_2$) or -$CH_2CH_2OH$ and $R_2$ is alkyl($C_1$-$C_{18}$); alkyl($C_1$-$C_{18}$) substituted by 1 hydroxyl, 1 alkoxy($C_1$-$C_4$), 1 piperidino or 1 morpholino substituent; cyclohexyl; phenylalkyl($C_7$ or $C_8$); phenylalkyl($C_7$ or $C_8$) substituted on the phenyl nucleus by 1 or 2 alkyl($C_1$-$C_4$) and/or 1 hydroxyl substituent; phenyl; phenyl substituted by 1 alkyl($C_1$-$C_{12}$), 1 chlorine, 1 phenyl or 1 phenyl substituted by 1 hydroxyl and/or 1 or 2 alkyl($C_1$-$C_4$) substituents;

or $R_1$ and $R_2$ together with the -NH- group to which they are bound form a piperidine, morpholine, pyrrolidine or imidazolidine ring, $R_3$ is alkyl($C_1$-$C_{22}$); alkyl($C_1$-$C_{21}$)thio-alkyl($C_1$-$C_{21}$) with $C_2$-$C_{22}$ in the aggregate thereof; alkyl($C_1$-$C_4$) substituted by 1 or 2 chlorines; cycloalkyl($C_5$-$C_{12}$); cycloalkyl($C_5$-$C_{11}$)alkyl($C_1$-$C_7$) with $C_6$-$C_{12}$ in the aggregate thereof; phenylalkyl($C_7$-$C_{12}$); phenylalkyl($C_7$-$C_{12}$) substituted on the phenyl nucleus thereof by 1 or 2 hydroxyl and/or 1 or 2 alkyl($C_1$-$C_{12}$), 1 cycloalkyl($C_5$-$C_{12}$) or 1 cycloalkyl($C_5$-$C_{11}$)alkyl($C_1$-$C_7$) with $C_6C_{12}$ in the aggregate thereof; phenyl; phenyl substituted by 1 or 2 halogen, 1 cyano, 1 meta- or para-hydroxyl, 1 or 2 alkyl($C_1$-$C_{12}$), 1 or 2 alkoxy($C_1$-$C_{12}$), 1 phenyl and/or 1 $R_6$-O- or $R_6$-$SO_2$- substituent wherein $R_6$ is phenyl or phenyl substituted by 1 or 2 alkyl($C_1$-$C_8$) substituents having 1 to 3 substituents and a maximum of $C_{18}$ in the aggregate of the substituents; or a heterocyclic substituent selected from furyl, thienyl, benzothienyl, indolyl, pyridyl and quinoxalinyl unsubstituted or substituted by 1 or 2 halogen, 1 or 2 alkyl($C_1$-$C_4$) and/or 1 or 2 alkoxy($C_1$-$C_4$) substituents with a maximum of 2 substituents;

$R_4$ and $R_5$ are each, independently, alkyl($C_1$-$C_8$), phenyl or phenyl substituted by 1 halogen and/or 1 or 2 alkyl($C_1$-$C_4$) substituents, and p is 1 when the amine ligand is bidentate and p is 2 when the amine ligand is monodentate, i.e. p is 1 only when one or both of $R_1$ and $R_2$ are hydroxyalkyl.

Further preferred are the complexes of formula Ib

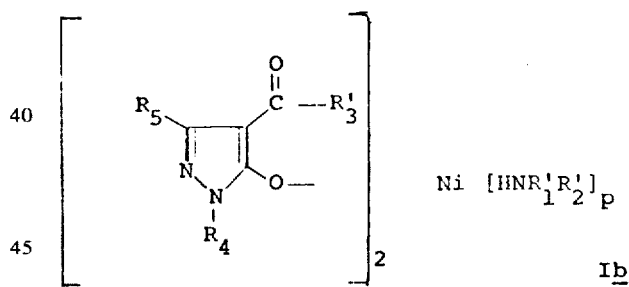

wherein either $R_1'$ is hydrogen or $C_1$ or $C_2$ alkyl, and $R_2'$ is one of the monovalent significances of $R_2$ and preferably is alkyl($C_1$-$C_{18}$), 2-hydroxyethyl, cyclohexyl, benzyl, phenyl or phenyl substituted by 1 alkyl ($C_1$-$C_{12}$), or $R_1'$ and $R_2'$ together with the -NH- group to which they are bound, form a piperidine, morpholine, pyrrolidine or imidazolidine ring, preferably a piperidine or morpholine ring, $R_3'$ is alkyl($C_1$-$C_{18}$); cycloalkyl($C_6$-$C_8$); phenylalkyl($C_7$-$C_{10}$); phenylalkyl($C_7$-$C_{10}$) substituted on the phenyl nucleus by 1 hydroxy and/or 1 or 2 alkyl($C_1$-$C_6$) substituents; phenyl; phenyl substituted by 1 or 2 halogen, 1 m- or p-hydroxyl, 1 or 2 alkyl($C_1$-$C_8$), 1 or 2 alkoxy($C_1$-$C_8$) and/or 1 phenyl substituent, with 1 to 3 substituents and a maximum of $C_{12}$ in the aggregate of the substituents;

furyl, thienyl or benzothienyl; or furyl, thienyl or benzothienyl substituted by 1 or 2 halogen or 1 alkyl($C_1$-$C_4$) substituent; and preferably has one of the significances of $R_3''$ as defined below, and $R_4$, $R_5$ and p are as defined above.

Still further preferred are the complexes of formula Ic,

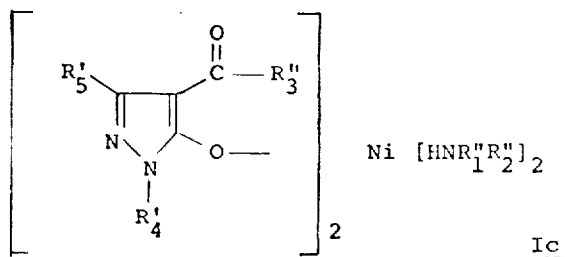

wherein either $R_1''$ is hydrogen and
$R_2''$ is alkyl($C_1$-$C_{18}$), cyclohexyl, benzyl, phenyl or phenyl substituted by 1 alkyl($C_1$-$C_{12}$), or $R_1''$ and $R_2''$, together with the -NH- group to which they are bound, form a morpholine ring,
$R_3''$ is alkyl($C_3$-$C_{18}$); cyclohexyl; phenylethyl; phenylethyl substituted on the phenyl nucleus by 1 hydroxyl and/or 1 or 2 alkyl($C_1$-$C_4$) substituents; phenyl; phenyl substituted by 1 chlorine, 1 m- or p-hydroxyl, 1 or 2 alkyl($C_1$-$C_4$), 1 alkoxy($C_1$-$C_4$) and/or 1 phenyl substituent, with 1 to 3 substituents and a maximum of $C_{12}$ in the aggregate of the substituents; furyl, thienyl or benzothienyl; or furyl, thienyl or benzothienyl substituted by 1 chlorine or 1 $C_1$ or $C_2$ alkyl substituent;
$R_4'$ is methyl, phenyl or phenyl substituted by 1 alkyl($C_1$-$C_4$), and $R_5'$ is alkyl($C_1$-$C_4$) or phenyl.

Of particular interest are the complexes of formula Id,

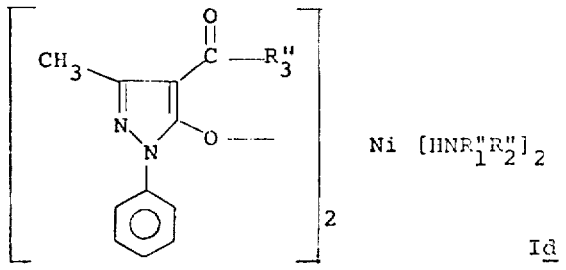

wherein $R_1''$, $R_2''$ and $R_3''$ are as defined above.

By the term "halogen" as employed herein is meant chlorine or bromine, preferably chlorine.

By the term "alkyl" as employed herein where this contains more than two carbon atoms is meant straight or branched chain primary, secondary, or where appropriate, tertiary alkyl.

When $R_1$ and $R_2$ together with the -NH- group to which they are bound form a heterocyclic ring, this is preferably a piperidine or morpholine ring and more preferably a morpholine ring.

When $R_2$ is alkyl, this is preferably unsubstituted.

When $R_2$ is substituted alkyl, this is preferably hydroxyl substituted alkyl($C_2$-$C_4$) and is especially 2-hydroxyethyl.

When $R_2$ is unsubstituted or substituted phenylalkyl, this is preferably unsubstituted or substituted benzyl and is in particular unsubstituted benzyl.

When $R_2$ is substituted phenyl, this is preferably phenyl substituted by 1 alkyl($C_1$-$C_{12}$).

When $R_3$ is alkyl, this is preferably ($C_3$-$C_{18}$) alkyl, e.g. ($C_8$-$C_{17}$)alkyl.

When $R_3$ is cycloalkyl, this is preferably cyclohexyl.

When $R_3$ is unsubstituted or substituted phenylalkyl, this is preferably unsubstituted or substituted phenylethyl. The substituents on the phenyl ring thereof are preferably 1 hydroxyl and/or 1 or 2 alkyl($C_1$-$C_4$) substituents.

When $R_3$ is substituted phenyl, this is preferably phenyl substituted by 1 chlorine, 1 m- or p-hydroxyl, 1 or 2 alkyl($C_1$-$C_4$), 1 alkoxy($C_1$-$C_4$) and/or 1 phenyl substituent.

When $R_3$ is heterocycle, this is preferably bonded through the 2-position thereof, e.g. thien-2-yl.

When $R_3$ is a substituted heterocycle, this is preferably substituted by 1 chlorine or 1 alkyl($C_1$ or $C_2$).

When either of $R_4$ and $R_5$ are alkyl, this is preferably, independently, alkyl($C_1$-$C_4$), particularly methyl.

When either of $R_4$ and $R_5$ are substituted phenyl, this is preferably, independently, phenyl substituted by 1 alkyl($C_1$-$C_4$).

Preferably $R_1$ has one of the significances of $R_1'$, especially $R_1''$, and is in particular hydrogen.

Preferably $R_2$ has one of the significances of $R_2'$ and more preferably of $R_2''$, e.g. n-butyl.

Preferably $R_3$ has one of the significances of $R_3'$, and especially $R_3''$.

Preferably $R_4$ has one of the significances of $R_4'$ and is in particular phenyl.

Preferably $R_5$ has one of the significances of $R_5'$ and is more preferably alkyl, especially methyl.

Preferably the amine ligand(s) of the complexes(I) are of the formula $[NHR_1R_2]_p$.

Preferably the amine is a monodentate ligand, i.e. p is preferably 2.

The complexes (I) are produced in accordance with a further aspect of the present invention by complexing the corresponding amine with the corresponding pyrazol-(5)-oxy nickel complex or, together with the corresponding pyrazolone-(5) compound, in free or alkali metal salt form, with a complexable nickel salt, preferably the latter.

The reaction is effected in known manner, in a solvent such as an alcohol, e.g. methanol, ethanol or n-propanol, preferably at an elevated temperature, conveniently at the boiling temperature of the reaction mixture under reflux. The complex usually precipitates out on cooling. Precipitation may be initiated or accelerated by the addition of water.

Examples of complexable nickel salts are the chloride, acetate, sulphate and tartrate salts.

The pyrazolone-(5) and amine compounds are either known or may be produced in manner known per se.

The complexes (I) are useful in the stabilization of sensitive material against the degradative effect of ultra-violet (U.V.) light.

Accordingly, the present invention provides a method of stabilizing sensitive material against the degradative effect of U.V. light which comprises "treating" said material with an effective amount of a complex (I).

By the term "treating" as employed herein is meant surface coating or incorporating the complex on or in, respectively, the material. The complex is preferably incorporated in the body of the material and more preferably is uniformly distributed therein.

Sensitive materials to which the method of the invention is suited include natural and synthetic polymeric materials such as natural rubber, natural cellulose, e.g. cotton, and natural polyamides, e.g. wool and silk, and synthetic polymeric materials such as synthetic polyalkylenes especially polyethylene and polypropylene, polyesters especially polyethylene terephthalates, cellulose acetobutyrate, polyvinylchloride, polymethyl methacrylates, polyphenylene oxides, polystyrene, polyurethanes, polycarbonates, polyacrylonitriles, polyamides, such as nylon, and polypropylene oxide and including synthetic co- and terpolymers such as copolymers of styrene and acrylonitrile or of styrene and butadiene and terpolymers of acrylonitrile, butadiene and styrene (ABS) and acrylic esters, styrene and acrylonitrile.

Preferably, the material treated comprises synthetic polymeric material, particularly polyethylene, polypropylene, polyester, polyamide, polyurethane, polyacrylonitrile, copolymers of styrene and acrylonitrile or styrene and butadiene, acrylonitrilebutadiene-styrene terpolymers and terpolymers of acrylic esters, styrene and acrylonitrile.

The stabilized materials may be in solid forms, e.g. panels, rods, coatings, sheets, films, tapes, fibres, granules or powders or in liquid or paste forms, e.g. solutions or emulsions.

The material to be stabilized may be treated in conventional manner.

In the treatment of kneadable solid materials, one important embodiment of the method of the invention comprises intimately mixing the complexes with a particulate, e.g. granular, form of material, e.g. polypropylene, in a kneader. The material may thereafter be formed into the required shape, e.g. by extrusion or injection moulding.

In the treatment of synthetic polymeric materials, a further important embodiment of the method of the invention comprises mixing the monomer or prepolymer with the complex prior to polymerization.

The amount of complex employed in the method of the invention will naturally vary depending, for example on the complex employed, the material to be treated and the mode of treatment. However, in general, satisfactory results may be obtained when the amount of complex employed is in the range 0.01 to 5%, preferably 0.05 to 1% of the weight of the material to be treated.

In the following Examples the parts and percentages are by weight. The temperatures are in degrees centigrade. The structures of the obtained compounds are verified by microanalysis and spectral analysis.

EXAMPLE 1

2.48 g of nickel acetate tetrahydrate are added at reflux temperature to 7.1 g of 1-phenyl-3-methyl-4-lauroyl-pyrazolone-(5) and 7.4 g of dodecylamine in 50 ml of methanol. The mixture is kept at reflux temperature for 20 minutes. The precipitated blue-green complex is suctioned off at room temperature, washed with water and dried. The complex of formula

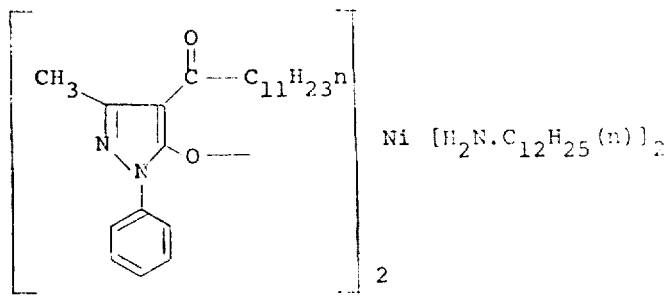

is obtained. M.P. 96°–98°.

EXAMPLE 2

The complex of the formula

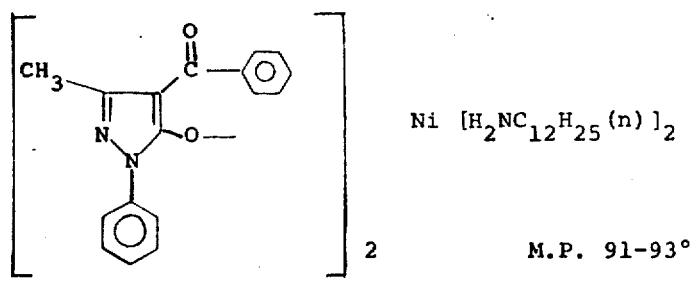

M.P. 91–93° is produced in analogous manner to that described in Example 1. After refluxing, the methanol solvent is distilled off and the residue taken up in petroleum ether (B.P. 100°–120°), washed with water, dried and the ether distilled off.

The complexes set out below are produced in analogous manner to that described in Example 1.

TABLE 1

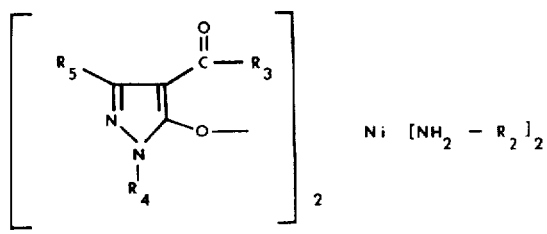

| Ex. No. | $R_3$ | $R_2$ | $R_4$ | $R_5$ | M.P. |
|---|---|---|---|---|---|
| 3 | phenyl | $-C_4H_9(n)$ | phenyl | $-CH_3$ | 160–165° |
| 4 | '' | $-C_8H_{17}(n)$ | '' | '' | 118–121° |
| 5 | '' | $-C_{18}H_{37}(n)$ | '' | '' | resin |
| 6 | $-C_{11}H_{23}(n)$ | phenyl | '' | '' | 91–94° |
| 7 | 4-tolyl | $-C_{12}H_{25}(n)$ | '' | '' | 159–161° |
| 8 | '' | $-C_4H_9(n)$ | '' | '' | >200° |
| 9 | biphenyl | phenyl | '' | '' | >250° |
| 10 | '' | $-C_{12}H_{25}(n)$ | '' | '' | 145–147° |
| 11 | $CH_3O$-phenyl | phenyl | '' | '' | 140–146° |
| 12 | HO-(t-butyl)phenyl | '' | '' | '' | 141–147° |
| 13 | phenyl | phenyl | '' | '' | 190–193° |
| 14 | t-butylphenyl | '' | '' | '' | >200° |
| 15 | $-H$ | $-C_{12}H_{25}(n)$ | '' | '' | 94–97° |
| 16 | '' | benzyl | '' | '' | 230–231° |
| 17 | '' | phenyl | '' | '' | 198–203° |
| 18 | phenyl | biphenyl | '' | '' | 237–239° |
| 19 | '' | benzyl | '' | '' | 125–129° |
| 20 | '' | $-C_6H_4-C_{12}H_{25}(n)$ | '' | '' | resin |
| 21 | $-C_{15}H_{31}(n)$ | phenyl | '' | '' | 98–102° |
| 22 | $-C_{17}H_{35}(n)$ | '' | '' | '' | 92–95° |
| 23 | t-butylphenyl | benzyl | '' | '' | >200° |
| 24 | '' | biphenyl | '' | '' | >200° |
| 25 | '' | $-C_6H_4-C_{12}H_{25}(n)$ | '' | '' | resin |
| 26 | phenyl | (t-butyl)(OH)phenyl | phenyl | '' | 98–107° |
| 27 | $-C_9H_{19}(n)$ | phenyl | '' | '' | 106–107° |
| 28 | phenyl | benzyl | '' | phenyl | 110–120° |
| 29 | $-C_9H_{19}(n)$ | '' | '' | $-CH_3$ | 97–100° |

TABLE 1-continued
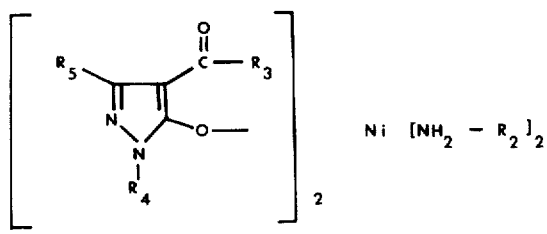
| Ex. No. | $R_3$ | $R_2$ | $R_4$ | $R_5$ | M.P. |
|---|---|---|---|---|---|
| 30 | -C₆H₄-+ | —C₄H₉(n) | -C₆H₅ | -C₆H₅ | 245–250° |
| 31 | -C₆H₄-CH₃ | '' | '' | '' | 108–130° |
| 32 | —C₈H₁₇(n) | '' | '' | '' | 113–114° |
| 33 | '' | -C₆H₅-CH₂- | '' | '' | 124–126° |
| 34 | -C₆H₅ | —C₄H₉(n) | CH₃-C₆H₄- | —CH₃ | 175–180° |
| 35 | -C₆H₄-+ | —C₄H₉(n) | -C₆H₅ | nC₃H₇— | 237–242° |
| 36 | '' | -C₆H₁₁- | '' | '' | 248–250° |
| 37 | '' | -C₆H₅-CH₂- | '' | '' | 235–237° |
| 38 | —C₉H₁₉(n) | -C₆H₁₁- | '' | nC₃H₇— | 99–102° |
| 39 | '' | —C₈H₁₇(n) | '' | '' | 94–105° |
| 40 | thienyl | -CH₂-C₆H₅ | '' | CH₃ | 90–105° |
+ = —C(CH₃)₃
EXAMPLE 41
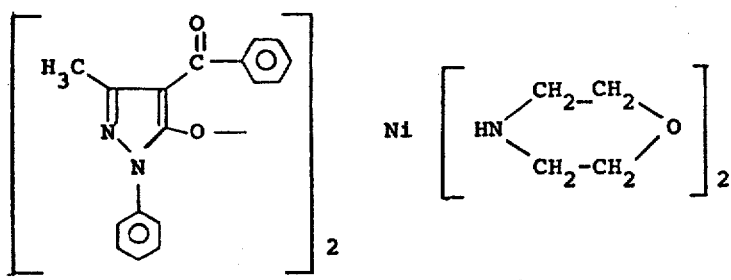
EXAMPLE 42
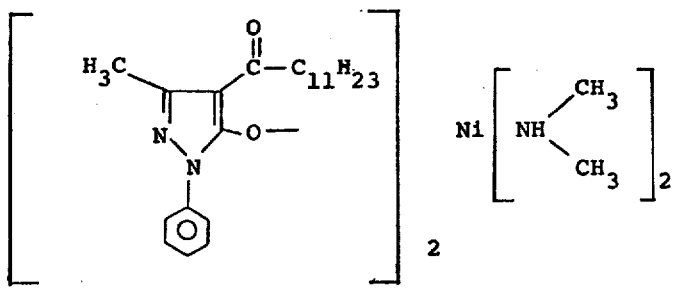
M.P. 134–137°C

TABLE 2

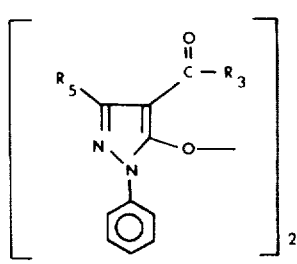

| Ex. No. | R₃ | R₅ | M.P. |
|---|---|---|---|
| 43 | C₉H₁₉(n) | —CH₃ | >200° |
| 44 | —C₁₁H₂₃(n) | —CH₃ | ~200° |
| 45 | —⟨O⟩ | —CH₃ | >200° |
| 46 | —⟨O⟩— | —CH₃ | >200° |
| 47 | —⟨O⟩— | —C₃H₇(n) | >200° |
| 48 | —⟨O⟩— | —⟨O⟩ | >200° |

EXAMPLE 49

52.2 g 1-phenyl-3-methyl-pyrazolone-(5) and 19.8 g of CaO are added to 180 g of dioxane. With stirring and over the course of 1 hour at 90°, 59.0 g of para-tert.butyl-benzoyl chloride are added to the mixture. After completion of the reaction, the dioxane is distilled off and the residue taken up in 100 g of toluene, 35 g of concentrated HCl and 90 g of water and stirred for 30 minutes at 90° until the organic phase separates. The organic phase is separated, washed with water until neutral and finally the toluene distilled off. The dark brown residue is then reacted with 35.6 g nickel chloride hexahydrate in 300 g of methanol to produce a green solution. The green solution is reacted with 60 g of cyclohexylamine with cooling over 10 minutes in an ice bath, the reaction product precipitating out. The product is washed with methanol and then water and dried at 90°C. The following compound

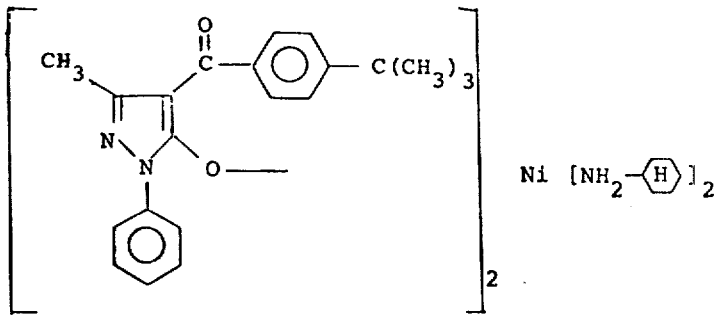

(M.P. 242°–250°) is obtained.

The compounds of Examples 1 to 48 can also be produced in analogous manner to that described in Example 49.

METHOD EXAMPLE

3 Samples of unstabilized polypropylene and 0.5% by weight of the complex of Example 1, 2 and 14 are intimately kneaded on a roll mill at 180°. Each sample is extruded into sheets of 0.3 mm thickness. Specimens of the sheets were tested for stability in the "Klimatest" apparatus by the De La Rue method at 40° and 75% relative atmospheric humidity, with thorough ventilation and irradiation by 16 sun lamps and 16 black lamps of Philips manufacture. The degree of stabilization is determined by comparing the effect of the polypropylene sample with the effect obtained with polypropylene containing no complex. The result in each case showed a stabilizing effect by the complex.

Specimens of an unstabilized polyvinyl chloride sheet and a sheet containing 0.5% of the complex of Example 10 in Table 1 were tested in analogous manner in the "Klimatest" apparatus with a similar result.

Analogous results are obtained for polyethylene, acrylonitrile-butadiene-styrene terpolymer, polyethylene terephthalate, cellulose acetobutyrate, polyamine 6, polystyrene, polycarbonate and polyurethane.

We claim:

1. A nickel complex of the formula

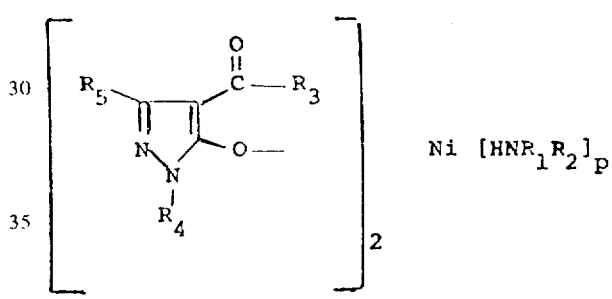

wherein either
$R_1$ is hydrogen, alkyl($C_1$-$C_8$) or -$CH_2CH_2OH$ and $R_2$ is alkyl($C_1$-$C_{18}$); alkyl($C_1$-$C_{18}$) substituted by 1 hydroxyl, 1 alkoxy($C_1$-$C_4$), 1 piperidino or 1 morpholino substituent; cyclohexyl; phenylalkyl($C_7$ or $C_8$); phenylalkyl($C_7$ or $C_8$) substituted on the phenyl nucleus by 1 or 2 alkyl($C_1$-$C_4$) and/or 1 hydroxyl substituent; phenyl; phenyl substituted by 1 alkyl($C_1$-$C_{12}$), 1 chlorine, 1 phenyl or 1 phenyl substituted by 1 hydroxyl and/or 1 or 2 alkyl($C_1$-$C_4$) substituents;

or $R_1$ and $R_2$ together with the -NH- group to which they are bound form a piperidine, morpholine, pyrrolidine or imidazoline ring, $R_3$ is alkyl($C_1$-$C_{22}$); alkyl($C_1$-$C_{21}$)thio-alkyl($C_1$-$C_{21}$) with $C_2$-$C_{22}$ in the aggregate thereof; alkyl($C_1$-$C_4$) substituted by 1 or 2 chlorines; cycloalkyl($C_5$-$C_{12}$); cycloalkyl($C_5$-$C_{11}$)alkyl($C_1$-$C_7$) with $C_6$-$C_{12}$ in the aggregate thereof; phenylalkyl($C_7$-$C_{12}$); phenylalkyl($C_7$-$C_{12}$) substituted on the phenyl nucleus thereof by 1 or 2 hydroxyl and/or 1 or 2 alkyl($C_1$-$C_{12}$), 1 cycloalkyl($C_5$-$C_{12}$) or 1 cycloalkyl($C_5$-$C_{11}$)alkyl($C_1$-$C_7$) with $C_6$-$C_{12}$ in the aggregate thereof; phenyl; phenyl substituted by 1 or 2 halogen, 1 cyano, 1 meta- or para-hydroxyl, 1 or 2 alkyl($C_1$-$C_{12}$), 1 or 2 alkoxy($C_1$-$C_{12}$), 1 phenyl and/or 1 $R_6$-O- or $R_6$-$SO_2$-substituent wherein $R_6$ is phenyl or phenyl substituted by 1 or 2 alkyl($C_1$-$C_8$) substituents having 1 to 3 substituents and a maximum of $C_{18}$ in the aggregate of the substituents; or a heterocyclic substituent selected from furyl, thienyl, benzothienyl, indolyl, pyridyl and quinoxalinyl unsubstituted or substituted by 1 or 2 halogen, 1 or 2 alkyl($C_1$-$C_4$) and/or 1 or 2 alkoxy($C_1$-$C_4$) substituents with a maximum of 2 substituents;

$R_4$ and $R_5$ are each, independently, alkyl($C_1$-$C_8$), phenyl or phenyl substituted by 1 halogen and/or 1 or 2 alkyl($C_1$-$C_4$) substituents, and p is 1 when the amine ligand is bidentate and p is 2 when the amine ligand is monodentate.

2. A nickel complex according to claim 1 of the formula

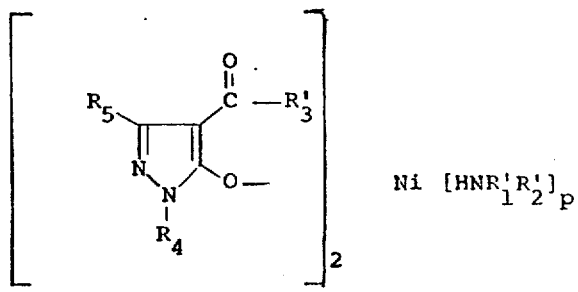

wherein either $R_1'$ is hydrogen or $C_1$ or $C_2$ alkyl, and $R_2'$ is one of the monovalent significances of $R_2$, or $R_1'$ and $R_2'$ together with the -NH- group to which they are bound, form a piperidine, morpholine, pyrrolidine or imidazolidine ring, $R_3'$ is alkyl($C_1$-$C_{18}$); cycloalkyl($C_6$-$C_8$); phenylalkyl($C_7$-$C_{10}$); phenylalkyl($C_7$-$C_{10}$) substituted on the phenyl nucleus by 1 hydroxyl and/or 1 or 2 alkyl($C_1$-$C_6$) substituents; phenyl; phenyl substituted by 1 or 2 halogen, 1 m- or p-hydroxyl, 1 or 2 alkyl($C_1$-$C_8$), 1 or 2 alkoxy($C_1$-$C_8$;) and/or 1 phenyl substituent, with 1 to 3 substituents and a maximum of $C_{12}$ in the aggregate of the substituents; furyl, thienyl or benzothienyl; or furyl, thienyl or benzothienyl substituted by 1 or 2 halogen or 1 alkyl ($C_1$-$C_4$) substituent, and $R_4$, $R_5$ and p are as defined in claim 1.

3. A nickel complex according to claim 2, of the formula

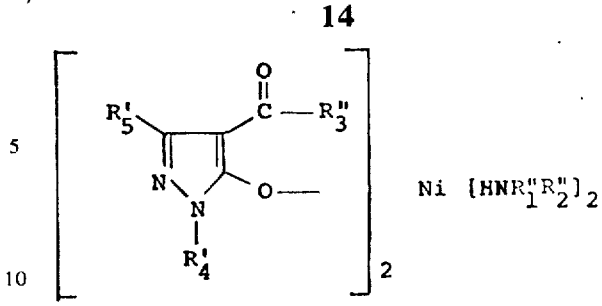

wherein either $R_1''$ is hydrogen and $R_2''$ is alkyl($C_1$-$C_{18}$), cyclohexyl, benzyl, phenyl or phenyl substituted by 1 alkyl($C_1$-$C_{12}$), or $R_1''$ and $R_2''$, together with the -NH- group to which they are bound, form a morpholine ring, $R_3''$ is alkyl($C_3$-$C_{18}$); cyclohexyl; phenylethyl; phenylethyl substituted on the phenyl nucleus by 1 hydroxyl and/or 1 or 2 alkyl($C_1$-$C_4$) substituents; phenyl; phenyl substituted by 1 chlorine, 1 m- or p-hydroxyl, 1 or 2 alkyl($C_1$-$C_4$), 1 alkoxy($C_1$-$C_4$) and/or 1 phenyl substituent, with 1 to 3 substituents and a maximum of $C_{12}$ in the aggregate of the substituents; furyl, thienyl or benzothienyl; or furyl, thienyl or benzothienyl substituted by 1 chlorine or 1 $C_1$ or $C_2$ alkyl substituent;

$R_4'$ is methyl, phenyl or phenyl substituted by 1 alkyl($C_1$-$C_4$), and $R_5'$ is alkyl($C_1$-$C_4$) or phenyl.

4. A nickel complex according to claim 3 of the formula

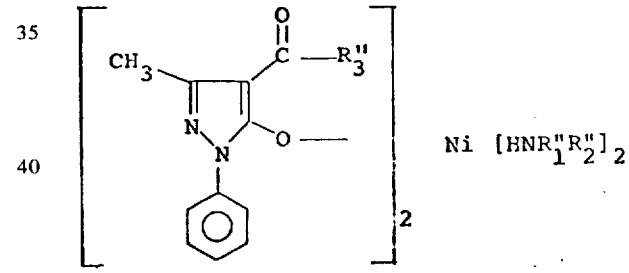

wherein $R_1''$, $R_2''$ and $R_3''$ are as defined in claim 3.

5. A nickel complex according to claim 4, wherein $R_1''$ is hydrogen.

6. A nickel complex according to claim 5, wherein $R_2''$ is n-dodecyl and $R_3''$ is phenyl.

7. A nickel complex according to claim 5, wherein $R_2''$ is cyclohexyl and $R_3''$ is p-tert.butyl phenyl.

8. A nickel complex according to claim 5, wherein $R_2''$ is benzyl and $R_3''$ is p-tert.butyl phenyl.

9. A nickel complex according to claim 5, wherein $R_2''$ is n-butyl and $R_3''$ is p-tert.butyl phenyl.

10. A nickel complex according to claim 5, wherein $R_2''$ is n-dodecyl and $R_3''$ is p-tert.butyl phenyl.

11. A nickel complex according to claim 5, wherein $R_2''$ is n-dodecyl and $R_3''$ is cyclohexyl.

12. A nickel complex according to claim 1, wherein $R_1$ is hydrogen, $R_2$ is 2-hydroxyethyl, $R_4$ is phenyl and $R_5$ is methyl.

13. A nickel complex according to claim 12, wherein $R_3$ is p-tert. butyl phenyl.

14. A nickel complex according to claim 12, wherein $R_3$ is n-nonyl.

15. A nickel complex according to claim 12, wherein $R_3$ is n-undecyl.

* * * * *